United States Patent [19]
Pecor et al.

[11] Patent Number: 5,843,002
[45] Date of Patent: Dec. 1, 1998

[54] GUIDE WIRE DISPENSER APPARATUS AND METHOD

[75] Inventors: Robert Pecor; Manoucher Miraki, both of Aliso Viejo; Donald Bobo, Jr., Orange, all of Calif.

[73] Assignee: Baxter International Inc., Deerfield, Ill.

[21] Appl. No.: 662,748

[22] Filed: Jun. 10, 1996

[51] Int. Cl.⁶ ........................................................ A61B 5/00
[52] U.S. Cl. .............................. 600/585; 604/96; 604/280
[58] Field of Search ...................................... 128/772, 657, 128/658; 604/95, 96, 280, 281, 282

[56] References Cited

U.S. PATENT DOCUMENTS

| | | |
|---|---|---|
| 3,416,531 | 12/1968 | Edwards . |
| 3,521,620 | 7/1970 | Cook . |
| 3,561,445 | 2/1971 | Katerndahl . |
| 3,682,173 | 8/1972 | Center . |
| 3,774,605 | 11/1973 | Jewett . |
| 3,826,256 | 7/1974 | Smith . |
| 3,835,854 | 9/1974 | Jewett . |
| 3,847,140 | 11/1974 | Ayella . |
| 3,995,628 | 12/1976 | Gula et al. . |
| 4,003,369 | 1/1977 | Heilman et al. . |
| 4,020,829 | 5/1977 | Willson et al. . |
| 4,080,706 | 3/1978 | Heilman et al. . |
| 4,160,451 | 7/1979 | Chittenden . |
| 4,173,228 | 11/1979 | Van Steenwyk et al. . |
| 4,205,675 | 6/1980 | Vaillancourt . |
| 4,215,703 | 8/1980 | Willson . |
| 4,274,408 | 6/1981 | Nimrod . |
| 4,311,139 | 1/1982 | Smith . |
| 4,342,313 | 8/1982 | Chittenden . |
| 4,397,091 | 8/1983 | Gustavson et al. . |
| 4,417,886 | 11/1983 | Frankhouser et al. . |
| 4,425,908 | 1/1984 | Simon . |
| 4,534,363 | 8/1985 | Gold . |
| 4,540,404 | 9/1985 | Wolvek . |
| 4,569,347 | 2/1986 | Frisbie . |
| 4,650,472 | 3/1987 | Bates . |
| 4,652,256 | 3/1987 | Vaillancourt . |
| 4,676,249 | 6/1987 | Arenas et al. . |
| 4,716,757 | 1/1988 | McGregor et al. . |
| 4,724,846 | 2/1988 | Evana, III . |
| 4,726,369 | 2/1988 | Mar . |
| 4,795,434 | 1/1989 | Kujawski . |
| 4,799,496 | 1/1989 | Hargreaves et al. . |
| 4,813,938 | 3/1989 | Raulerson . |
| 4,824,435 | 4/1989 | Giesy et al. . |
| 4,844,092 | 7/1989 | Rydell et al. . |

(List continued on next page.)

FOREIGN PATENT DOCUMENTS

| 0 587 984 | 3/1994 | European Pat. Off. . |
|---|---|---|
| 207358 | 12/1967 | U.S.S.R. . |

OTHER PUBLICATIONS

International Search Report dated Oct. 27, 1997 relating to corresponding application PCT/US97/08484.

*Primary Examiner*—Max Hindenburg
*Assistant Examiner*—Pamela L. Wingood
*Attorney, Agent, or Firm*—Terry L. Miller; Bruce M. Canter; Guy L. Cumberbatch

[57] ABSTRACT

A storage and dispensing apparatus for a springy guide wire used in medical procedures includes a coiled tubular portion defined by elongate tubing with a bore for receiving the guide wire. A ring section includes a tangential portion of the tubing defining an open end from which the guide wire may be dispensed. Adjacent to the tangential portion, the tubing defines a pair of spaced apart openings from which the guide wire respectively exits and reenters the tubing. Intermediate the pair of openings the tubing defines a curved external surface across which the guide wire runs externally of the tubing and is manually accessible for advancing and retracting movements impelled by a user's thumb, for example. The guide wire defines a pair of gentle S-shaped bends adjacent to the ends of the externally-exposed curved section, which bends cause the guide wire to engage sufficiently with the storage and dispensing apparatus to resist self-ejection.

38 Claims, 2 Drawing Sheets

U.S. PATENT DOCUMENTS

| | | |
|---|---|---|
| 4,854,325 | 8/1989 | Stevens . |
| 4,858,810 | 8/1989 | Intlekofer et al. . |
| 4,860,757 | 8/1989 | Lynch et al. . |
| 4,860,759 | 8/1989 | Lynch et al. .......................... 128/772 |
| 4,917,094 | 4/1990 | Lynch et al. . |
| 5,125,906 | 6/1992 | Fleck . |
| 5,186,179 | 2/1993 | MacEachern . |
| 5,273,042 | 12/1993 | Lynch et al. . |
| 5,282,479 | 2/1994 | Havran . |
| 5,325,746 | 7/1994 | Anderson ................................ 128/772 |
| 5,366,444 | 11/1994 | Martin .................................... 128/772 |
| 5,438,993 | 8/1995 | Lynch et al. . |
| 5,448,993 | 9/1995 | Lynch et al. . |
| 5,499,632 | 3/1996 | Hill, III et al. ........................ 128/772 |
| 5,507,300 | 4/1996 | Mukai et al. . |

GUIDE WIRE DISPENSER APPARATUS AND METHOD

BACKGROUND OF THE INVENTION

Field of the Invention

In a broad aspect, the present invention is related to the field of medical guide wires. More particularly, the present invention is directed to the field of guide wire storage, dispensing, and manipulation apparatus and methods used to store, transport, and dispense guide wires in any medical procedure utilizing a guide wire to introduce a device into a body. For example, the present invention may be used in connection with the intravascular placement of medical devices, particularly the placement of central venous catheters, percutaneous introducers, intravascular monitoring catheters and in the performance of angioplastic cardiac catheterization.

Related Technology

As the need to access the interior of the human body has expanded in order to diagnose, monitor, and treat a variety of medical conditions, numerous techniques have been developed to provide the attending physician and medical personnel with the ability to accurately position medical devices within a patient's body and to access seemingly remote areas within a patient's vasculature. One of the more popular techniques utilizes a simple, yet effective, medical device known as a guide wire. Medical guide wires range from inches to feet in length and typically are formed of surgical grade stainless steel or similar material. Because they are formed with very small diameters measured in the thousandths of an inch they are highly flexible; yet, because of the inherent stiffness and resiliency of the materials from which they are formed, physicians and medical personnel are able to easily insert and direct guide wires through tortuous vascular pathways or into body cavities and other locations.

By pushing and rotating the proximal end of the guide wire outside of the patient the physician is able to direct the distal end of the guide wire to the desired target site. Typically, the distal end of the guide wire is provided with a relatively soft, atraumatic flexible tip which may be formed of radiopaque material to facilitate fluoroscopic visualization of the guide wire as it is advanced within a patient's body. Once in place, a wide variety of medical devices may be directed to the target site along the guide wire by simply sliding a lumen or channel formed in the device over the guide wire to advance the device to the distal tip. Following placement of the device, the guide wire can be removed if desired.

One widely practiced method for the intravascular placement of guide wires and, subsequently, medical devices, is known as the modified Seldinger approach. Utilizing this technique, physicians or medical personnel first verify vascular access utilizing a syringe with an appropriately sized hypodermic needle. To verify that the needle has accessed the appropriate vascular pathway, the syringe is utilized to pull a visible sample of blood through the hypodermic needle where it can be observed by the physician. Following confirmation of vascular access, the syringe is removed leaving the appropriately gauged hypodermic needle in position within the vascular pathway. The physician then inserts the distal end of the guide wire into the hypodermic needle hub and then advances the remaining length of the guide wire intravascularly to the target site.

As those skilled in the art will appreciate, in order to access remote regions deep within a patient's vasculature or other body location, a correspondingly sized guide wire must be used. Additionally, if relatively lengthy medical devices are to be advanced effectively along the guide wire a correspondingly sized portion of the guide wire must extend out of the patient's body to allow the physician to thread the device onto the proximal end of the guide wire without losing control of the guide wire placement within the patient's body. As a result, it is not uncommon for guide wires to extend many feet in length. Thus, maintaining control of the lengthy guide wire during its placement and use can be complicated and awkward.

Early solutions to such problems relied upon the simple expedient of providing an additional pair of hands in the form of a medical assistant who would be charged with controlling the external portion of the guide wire as the guiding physician or medical personnel would advance and position the distal end of the guide wire within the patient. Though acceptable, this technique proved to be quite costly and added to the crowding and potential for confusion within the operating room and the intensive care environment. More recent approaches directed toward solving the problem of guide wire dispensing and control have utilized hand held devices to manipulate and store the guide wire.

U.S. Pat. No. 5,125,906, issued 30 Jun. 1992, to Phillip B. Fleck, is believed to disclose a hand-held device for feeding or dispensing a guide wire. The device according to the '906 patent appears to include a handle-like apparatus having a length of tubing forming a housing and opening for dispensing a guide wire. The handle defines a tubular barrel member opening to an axial bore from which the guide wire dispenses, and a tubular rear end member opening to an end of the tubing in which the guide wire is stored. Intermediate of the barrel and rear end portions is an open straight section at which manual access to the guide wire can be achieved by use of the thumb and forefinger of a physician. The distal end portion of the barrel member includes a rather small bore in which a J-end portion of the guide wire is straightened for insertion into a syringe or needle for feeding the guide wire into an artery of a patient.

Another conventional guide wire advancer is known in accord with U.S. Pat. No. 5,273,042, issued 28 Dec. 1993, to Arthus S. Lynch, et al. The '042 patent is believed to teach a guide wire storage and advance device in which a loop of tubing is terminated in a straight tangential portion leading to an open end of the tubing. At the open end of the tubing, a straightener member is receivable into an end portion of the tubing to be secured thereto. Adjacent to the straight tangential portion of the tubing, an opening is formed at which manual access to the guide wire may be had by use of the thumb.

U.S. Pat. No. 5,366,444, issued 22 Nov. 1994, to Geoffrey S. Martin is believed to disclose yet another conventional device for feeding a guide wire. The device of the '444 patent also appears to include a length of tubular material formed into a loop. At one end of the loop of tubular material, a discharge head is joined to the tubing and includes a guide opening and an outlet tip with a discharge opening. Formed between the guide opening and the discharge tip is a straight platform over which the guide wire slides and at which manual access to the guide wire may be made by the use of a thumb to advance and retract the guide wire.

Finally, EP publication 0 587 984 A1, dated 5 May 1993, is believed to disclose a guide wire dispenser device in which a coiled tubing is attached at one end to a handle portion having a guide bore for receiving the end of the coiled tubing, and a spaced away tip portion having a bore through which the guide wire passes. Between the guide bore and the tip is defined an essentially straight platform at which manual access to the guide wire may be had. The tip bore is apparently offset somewhat relative to the guide bore, and the handle portion has a pair of oppositely curved lower portions leading to a clip-like feature capturing the opposite end of the tubing, all apparently to enhance the ergonomics of the device.

A persistent problem with conventional guide wire storage and dispensing apparatus is that the guide wires are inherently springy and difficult to control with one hand. The storage and dispensing apparatus conventionally employs a length of coiled tubing to store the guide wire prior to its being dispensed into a patient during introduction or intravascular placement of a medical device. Further, the coefficient of friction between the guide wire and the tubing in which it is stored is not very high which complicates storage and dispensing of the wire. Low friction is to be expected, and is desirable in some respects, because the guide wire is dispensed from the device using only that purchase on the guide wire which can be gained by the application of manual pressure and friction with one or more fingers, usually with the thumb alone. On the other hand, this relatively low coefficient of friction allows the guide wire to creep out of the conventional dispensers due to its own springiness, and due to jostling which occurs in shipping and handling. In some cases, physicians have the experience of having the guide wire advance out of the dispenser, or self-eject, under the influence of its own springiness. In the event where the guide wire self-ejects and contacts non-sterile environmental surfaces the wire cannot thereafter be introduced into a patient because of the risk of infection and must be discarded.

Summary of the Invention

In view of the deficiencies of the conventional technology outlined above, it is a primary object for this invention to avoid one or more of the deficiencies of the prior art with a simple and inexpensive apparatus.

Yet another object for the present invention is to provide a storage, transport, and dispensing apparatus for a guide wire which prevents the guide wire from self-ejecting.

Still another object for this invention is to provide such a storage, transport, and dispensing apparatus for a guide wire in which the guide wire is required to form an arch or arcuate section having a slight reverse bend or arcuate bend at each end, and intermediate of which the guide wire is exposed for manual advancing and retracting access.

According to one embodiment, the present invention provides a storage and dispensing apparatus for a guide wire, the apparatus including a wrap of elongate tubing having a bore for receiving an elongate guide wire, a first end, a tangential portion extending from said wrap and terminating at an open second end, adjacent to said tangential portion the elongate tubing defining a pair of spaced apart apertures opening from the bore radially outwardly on the tubing, and an outer curved surface portion extending along the length dimension of the tubing intermediate of the pair of openings across which a curved portion of the guide wire may extend and be accessible for manual manipulation to advance and retract the guide wire through the open second end; and means for providing manual purchase on the wrap of tubing. The means for providing manual purchase may be config- ured as a handle, which also may include features for constraining the tubing in a spiral shape.

A better understanding of the present invention will be obtained from reading the following description of two preferred exemplary embodiments of the present invention when taken in conjunction with the appended drawing Figures, in which the same features (or features which are analogous in structure or function) are indicated with the same reference numeral throughout the several views. It will be understood that the appended drawing Figures and description here following relate only to one or more exemplary referred embodiments of the invention, and as such, are not exhaustive and do not imply a limitation on the invention. No such limitation on the invention is implied, and none is to be inferred.

BRIEF DESCRIPTION OF THE DRAWING FIGURES

FIG. 1 provides a fragmentary view showing a storage and dispensing apparatus according to the present invention in use by a physician to dispense a guide wire therefrom into a patient;

DETAILED DESCRIPTION OF TWO EXEMPLARY PREFERRED EMBODIMENTS OF THE INVENTION

Figure 1:
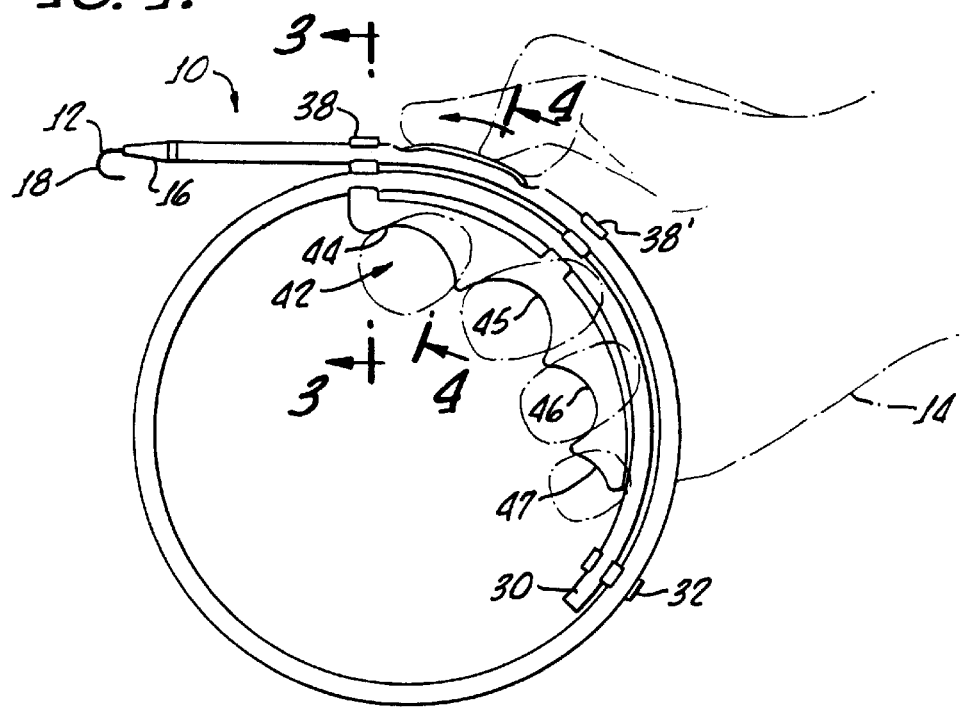
Figure 2:
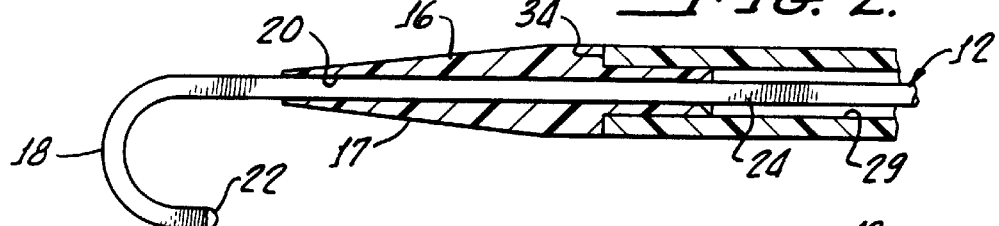
FIG. 2 is an enlarged fragmentary cross sectional view of a portion of the apparatus shown in FIG. 1.

Viewing FIG. 1, a storage and dispensing apparatus 10 for a guide wire 12 is seen in use by a physician 14 to dispense the guide wire via a hypodermic needle (not shown) into the vasculature of a patient (also not shown) preparatory to the introduction of a medical device. Those ordinarily skilled in the pertinent arts will understand that the hypodermic needle is inserted into a selected artery of the patient, and the guide wire 12 is introduced into the external portion of the needle via a tapered introducer tip 16 of the apparatus 10. This introducer tip defines a conically tapering outer surface 17. Conventionally, the guide wire 12 includes a J-shaped flexible resilient end portion 18. The introducer tip 16 defines a bore portion 20 at the distal termination of the surface 17 (best seen in FIG. 2) closely receiving the resilient end portion 18 of the guide wire 12.

Consequently, in use of the apparatus 10, the physician 14 may withdraw the J-shaped end portion 18 into the bores 20 and 29 (as will be explained), thus straightening this end portion preparatory to introducing the tapered introducer into the exterior portion of the hypodermic needle. As the guide wire 12 is advanced from the tip 16 and into the hypodermic needle (as also will be explained), the portion 18 is maintained relatively straight. Once into an artery or vein, the J-shaped tip facilitates steering the guide wire to a treatment site. It will be noted in FIG. 2 that the portion 18 of guide wire 12 terminates at a radiopaque marker tip 22 which is used to visualize the position of the end of the guide wire 12 within a patient. Those ordinarily skilled in the pertinent arts will also recognize that behind the resilient portion 18 the guide wire 12 includes a rather stiff, elongate and pushable, but springy and resilient, shaft portion 24. This shaft portion 24 is received into a coiled tubular part 26 of the apparatus 10. More properly, this tubular part 26 can be seen to be spiral wrapped on itself. The introducer tip 16 extends from a tangential portion of the coiled or spiral wrapped part 26.

In order to form the coiled tubular part 26, a length of tubing 28 is spiraled on itself as shown in FIG. 1, and adjacent to an end 30 thereof remote from the tip 16 is secured in a clip member 32. Thus, the clip member 32 secures to the tubing 28 as shown in FIG. 1 so that a spiral of this tubing is formed. In order to distinguish the outer wrap of this spiral from an inner wrap or wraps, the outer wrap is referenced with the numeral 28', and each successive wrap inwardly has an additional prime added. Thus, in the illustrated embodiment which has only a single inner wrap of tubing 28, the inner wrap is referenced with the numeral 28". Those ordinarily skilled in the pertinent arts will recognize that the apparatus 10 may include more than one spiral wrap of tubing, depending upon the length of the guide wire contained therein. The tubing 28 defines a bore or longitudinal inner passage 29.

Adjacent to an end 34 at which a portion of the tip member 16 is received into the tubing 28 (viewing FIG. 2), the inner wrap 28" and outer wrap 28' of tubing 28 are secured at two spaced apart locations into a combined handle and clip member 36 (hereinafter referred to simply as a handle member). As will be discussed, this handle member 36 provides for secure manual purchase on the apparatus 10, even in an operating room environment possibly including blood and other liquids which could make the apparatus 10 slippery and difficult to grasp and control precisely. Viewing FIGS. 1, 3, and 5, it can be seen that the handle member 36 includes a pair of spaced apart clip portions 38 and 38', each of which defines a respective radially spaced pair of recesses 40 and 40' for respectively receiving each wrap 28', and 28" of the tubing 28.

Thus, the clip portions 38 and 38' each define a pair of recesses 40 and 40'. The wraps 28', 28" of the tubing 28 are respectively snapped into the recesses 40 and 40' and are there retained by their own resilience in combination with the resilience of the clip portions 38 and 38'. It will be understood that the wraps 28', 28" of tubing 28 may also be otherwise or additionally secured into the recesses 40, 40' such as by the use of an adhesive, although this may not be required.

Handle portion 36 also includes an arcuate digit-engagement section 42 disposed within the spiral of tubing 28 and defining a plurality of tandem digit-engaging recess portions 44, 45, 46, and 47, each disposed one behind the other, respectively, for engagement by the index finger to the little finger of the user. The one clip portion 38 extends radially outwardly from a position generally in alignment with the index-finger recess 44, while the other clip portion 38' extends radially outwardly from a position of general alignment with the middle-finger recess 45. The digit-engaging recess portions 44–47 are joined to one another, and the forward portion 44 is disposed slightly closer to the tubing wraps 28' and 28" in order to improve the ergonomics of the apparatus 10.

Figure 3:
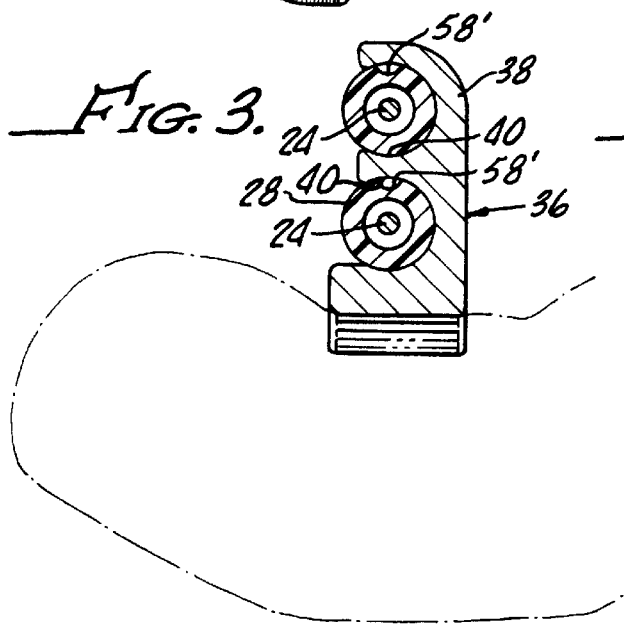
FIGS. 3 and 4 are respective enlarged fragmentary cross sectional views taken at the indicated planes of FIG. 1, and looking in the direction of the arrows.
Figure 5:
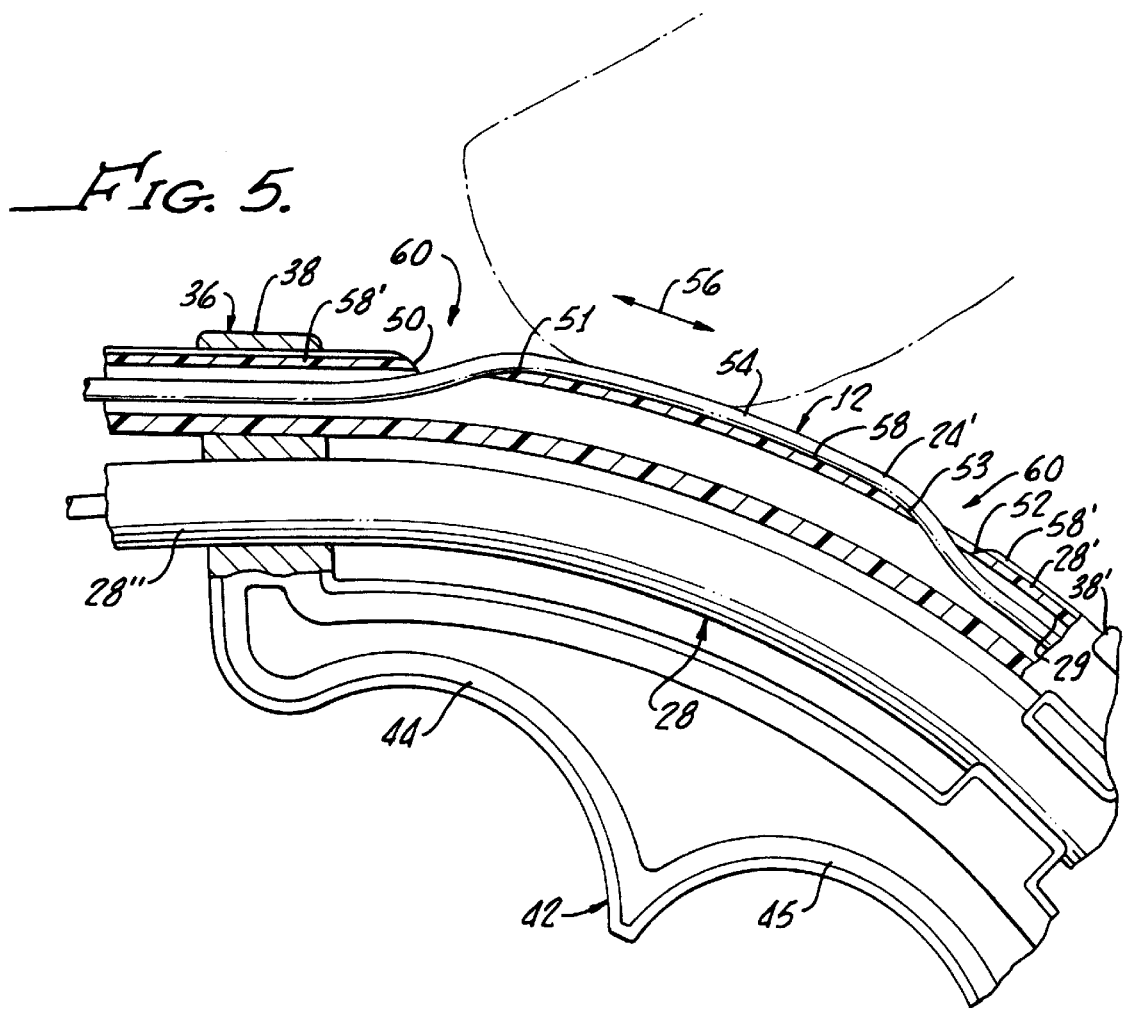
FIG. 5 is an enlarged fragmentary cross sectional view of a portion of the device shown in FIG. 1.

Each digit-engaging portion 44, 45, 46, and 47 defines a respective recess for receiving a finger of the physician's hand, as shown in FIGS. 1, 3, and 5. The fingers of the hand my be engaged by simply grasping the handle portion 36 with no need to insert fingers into rings or on opposite sides of a portion of tubing, as was the case with some of the conventional devices discussed above. This facility of the apparatus 10 improves the speed and utility of its use in an operating room environment. The tubing wraps 28' and 28" rearwardly of the digit-engaging portions 44–47 also cooperate with the handle portion 36 to provide an ergonomically appropriate and useful disposition of the apparatus 10 relative to a physician's hand and thumb for manipulating a guide wire.

Rearwardly of the clip portion 38 and forwardly of clip portion 38', the tubing 28 of the outer wrap 28' defines an outwardly disposed aperture 50 opening from the bore 29 radially outwardly on the tubing 28. Spaced rearwardly from the aperture 50 and forwardly of clip portion 38', the tubing 28 at outer wrap 28'defines another aperture 52 also opening radially from the bore 29 outwardly on the tubing 28. It will be noted that the apertures 50 and 52 are somewhat angular and are disposed angularly toward one another to define respective sloping surfaces 51 and 53. Intermediate of the openings 50 and 52, the tubing 28 defines an outer surface portion 54 across which the guide wire 12 extends. At this position guide wire 12 is available for manual access as depicted in FIGS. 1 and 5 to both advance and retract the guide wire, as illustrated by arrow 56 in FIG. 5. Guide wire shaft 24 extends out of the openings 50, 52, and runs lengthwise of tubing 28 along the curved surface portion 54, there to define a portion 24' accessible for manual contact and movement. Consequently, between the openings 50 and 52, as shown in FIG. 5, the tubing 28 at outer wrap 28' defines a bore portion 29' of bore 29 which is empty because the guide wire 12 is disposed outside of the tubing between the openings 50 and 52.

In order to provide lateral constraint of the guide wire 12 (i,e,. of shaft portion 24') between the openings 50 and 52, a groove 58 is formed on the curved outer surface 54 of the tubing 28 and extends between the openings 50 and 52.

Figure 4:
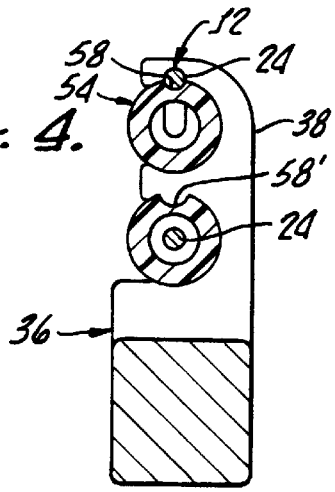

Groove 58 is disposed in the plane of the spiral of tubing 28, as shown in FIG. 4. The groove 58 may be formed by any convenient method. However, a particularly preferred way of forming groove 58 is to extrude the tubing 28 with a longitudinal groove 58' (best shown in FIGS. 3, 4, and 5) along its entire length, and to spiral wrap the tubing 28 to form the part 26 with the pre-formed groove 58' disposed radially outwardly, as shown in FIGS. 3, 4, and 5. When the openings 50 and 52 are formed in the tubing 28, a portion of the preformed groove 58' extends between these openings and defines groove 58. Because of the presence of groove 58, a portion 24' of the guide wire shaft 24 lays in this groove and is conveniently accessible with by physicians thumb to manually advance and retract the guide wire 12 with a single hand, as shown in FIGS. 1 and 5.

Also, because the guide wire shaft 24 forms a mild S-shaped bend 60 at each of the openings 50 and 52, the frictional engagement of guide wire 12 with tubing 28 is improved, and self-ejection of the guide wire from apparatus 10 is inhibited. That is, the engagement of guide wire 12 with tubing 28 is not so tenacious that the physician cannot easily advance and retract the guide wire manually, it is just sufficient that the guide wire 12 will not self-eject from storage and dispensing apparatus 10.

Figure 6:
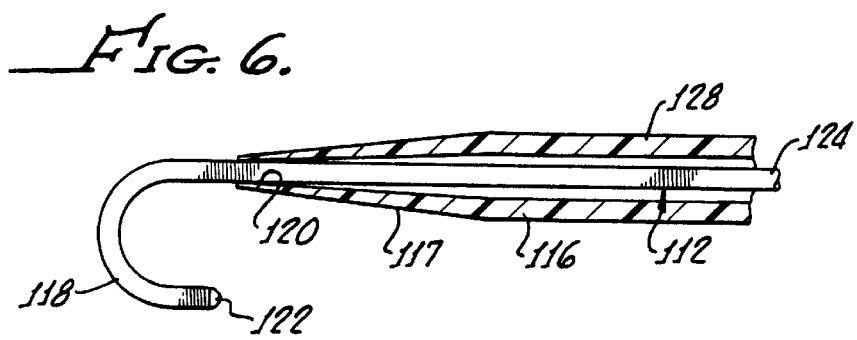
FIG. 6 is an enlarged fragmentary cross sectional view similar to that of FIG. 2, but showing an alternative embodiment of the invention.

Considering now FIG. 6, an alternative embodiment of the present guide wire storage and dispensing apparatus is depicted in fragmentary cross sectional view. In order to obtain reference numerals for use in describing this alternative embodiment of the invention, features which are the same as or equivalent in structure or function to those of the earlier embodiment are referenced with the same numeral used above, and increased by one-hundred (100). This view of FIG. 6 will be seen to be similar to that of FIG. 2, except that the distal end portion of the tubing 128 is integrally formed to define an introducer tip 116. The introducer tip 116 defines a conically tapering outer surface 117 terminating at a bore 120 slidably receiving the guide wire 112. This integral introducer tip offers the advantage of allowing insertion of the guide wire directly from the apparatus 12. In the event that a physician wants to manually manipulate the guide wire with two or more fingers, the apparatus 10 may simply be backed off slightly from the hypodermic needle, and access to the guide wire 112 is then possible intermediate of the device and the patient.

While the present invention has been depicted, described, and is defined by reference to two particularly preferred embodiments of the invention, such reference does not imply a limitation on the invention, and no such limitation is to be inferred. The invention is capable of considerable modification, alteration, and equivalents in form and function, as will occur to those ordinarily skilled in the pertinent arts. For example, while the present invention has been depicted and is described with reference to embodiments in which the elongate tubing is spiral wrapped on itself, the invention is not so limited. For example, the elongate tubing could be helically wrapped on itself, in which case the helical wraps of tubing would lay adjacent to one another in the user's hand. This arrangement would still allow the user to have access to the guide wire adjacent to an end of the coiled tubing. The depicted and described preferred embodiments of the invention are exemplary only, and are not exhaustive of the scope of the invention. Consequently, the invention is intended to be limited only by the spirit and scope of the appended claims, giving full cognizance to equivalents in all respects.

We claim:

1. A storage and dispensing apparatus for a guide wire, said apparatus comprising:
   a wrap of elongate tubing having a bore for receiving an elongate guide wire, a first end, an open second end, adjacent to said second end, said elongate tubing defining a pair of spaced apart apertures opening from said bore radially outwardly on said tubing, and an outer curved surface portion extending along the length dimension of said tubing intermediate of said pair of openings across which a curved portion of the guide wire may extend and be accessible for manual manipulation to advance and retract the guide wire through said open second end; and
   a handle attached to said wrap of tubing.

2. The storage and dispensing apparatus of claim 1 wherein said wrap of elongate tubing is formed as a spiral wrap.

3. The storage and dispensing apparatus of claim 1 wherein said pair of spaced apart apertures are each angulated toward the other to each provide a respective surface sloping toward the other of said pair of apertures and across which the guide wire is slidably disposed.

4. The storage and dispensing apparatus of claim 1 wherein said pair of spaced apart apertures are so disposed relative to one another that the guide wire defines an S-shaped bend between said bore and the curved manually-accessible portion of the guide wire, thereby to inhibit self-ejection of the guide wire from the apparatus.

5. The storage and dispensing apparatus of claim 1 wherein said elongate tubing defines a radially outwardly disposed groove extending between said pair of apertures, receiving the guide wire, and providing said curved surface across which the guide wire extends between said pair of apertures.

6. The storage and dispensing apparatus of claim 5 wherein said elongate tubing defines an elongate groove extending along the entire length thereof, said wrap of tubing being formed with said elongate groove disposed radially outwardly and between said pair of apertures defining said radially outwardly disposed groove between said pair of apertures for receiving said guide wire.

7. The storage and dispensing apparatus of claim 1 wherein said handle further includes a clip member including at least one clip portion defining a recess for receiving a wrap of said elongate tubing.

8. The storage and dispensing apparatus of claim 7 wherein said combined handle and clip member includes at least a pair of said clip portions each defining a respective recess for receiving a respective spiral wrap of said elongate tubing and being spaced circumferentially from one another along said wrap of tubing.

9. The storage and dispensing apparatus of claim 7 wherein said clip portion is configured to form a snap fit with said elongate tubing.

10. The storage and dispensing apparatus of claim 1 wherein said handle includes a digit-receiving recess portion disposed within said wrap of tubing and defining at least one recess for receiving a finger of a user of said apparatus.

11. The storage and dispensing apparatus of claim 10 wherein said digit-receiving portion defines a pair of said digit-receiving recess portions disposed one behind the other in tandem within said wrap of tubing, each for receiving a respective finger of a user of said apparatus.

12. The storage and dispensing apparatus of claim 11 wherein each of a forward two of said digit-receiving portions defines a respective one of a pair of clip portions extending radially outwardly therefrom, each one of said pair of clip portions extending radially outwardly from the respective one of said pair of pair of digit-receiving portions in general alignment with the respective index and middle fingers of a user of said apparatus and captively retaining at least one wrap of said tubing.

13. The storage and dispensing apparatus of claim 1 further including a tapered introducer tip member removably received at said open second end of said elongate tubing, said introducer tip member defining a bore closely passing the guide wire.

14. The storage and dispensing apparatus of claim 1, said elongate tubing further including a tangential portion extending from said wrap and being integrally formed into a tapered introducer tip portion defining a bore closely passing the guide wire and also defining said open second end of said elongate tubing.

15. A storage and dispensing apparatus for a guide wire, said apparatus comprising:
   a coiled tubular part including a spiral wrap of elongate tubing having a bore for receiving an elongate guide wire, said elongate tubing defining a first end, an open second end, and adjacent to said second end said elongate tubing defining a pair of spaced apart apertures opening from said bore radially outwardly on said tubing so that the guide wire may emerge from and reenter said tubing by said pair of apertures, said pair of apertures each being angulated toward the other to provide a respective surface sloping toward the other of said pair of apertures and across which the guide wire may be slidably disposed, between said pair of apertures said elongate tubing defining an outer curved surface portion extending along the length of said elongate tubing and across which a curved portion of the guide wire may extend between a pair of S-shaped bends in the guide wire to be manually accessible for manipulation advancing and retracting the guide wire through said open second end;

a combined handle and clip member including a clip portion defining a pair of clip recesses each for receiving a respective wrap of said elongate tubing, said handle and clip member also including at least one portion disposed within said wrap of tubing and defining at least one recess for receiving a finger of a user of said apparatus.

16. The storage and dispensing apparatus of claim 15 wherein said combined handle and clip member defines a tandem pair of said digit-receiving portions each for receiving a respective finger of a user of said apparatus within said wrap of tubing.

17. The storage and dispensing apparatus of claim 15 wherein said handle and clip member defines a tandem and adjacent pair of digit-receiving portions each for receiving a respective finger of a user of said apparatus within said wrap of tubing, and each of said tandem and adjacent pair of digit-receiving portions including a respective one of a pair of spaced apart clip portions each extending radially outwardly from the respective one of said pair of digit-receiving portions to captively retain a wrap of said tubing.

18. The storage and dispensing apparatus of claim 15 further including a tapered introducer tip member removably received at said open second end of said elongate tubing, said introducer tip member defining a bore closely passing the guide wire.

19. The storage and dispensing apparatus of claim 15, said elongate tubing further including a tangential portion extending from said wrap and being integrally formed into a tapered introducer tip portion defining a bore closely passing the guide wire and also defining said open second end of said elongate tubing.

20. The storage and dispensing apparatus of claim 15 wherein said elongate tubing defines a radially outwardly disposed groove extending between said pair of apertures, said outwardly disposed groove receiving the guide wire between said pair of apertures and guiding the guide wire for manual access thereto, said outwardly disposed groove further providing said curved surface across which the guide wire extends between said pair of apertures.

21. The storage and dispensing apparatus of claim 20 herein said elongate tubing defines an elongate groove extending along the entire length thereof, said wrap of tubing being formed with said elongate groove disposed radially outwardly and between said pair of apertures defining said radially outwardly disposed groove between aid pair of apertures for receiving the guide wire.

22. A method of providing for storage and manual dispensing of an elongate springy guide wire while inhibiting self-ejecting of the guide wire, said method comprising steps of:

providing a storage and dispensing apparatus for a guide wire configured as a wrap of elongate tubing having a bore for receiving the elongate guide wire, a first end, and an open second end, defining a pair of spaced apart apertures opening from said bore radially outwardly on said tubing adjacent to said second end, forming an outer curved surface portion on said elongate tubing extending along the length dimension of said tubing intermediate of said pair of openings, and extending the guide wire outwardly of the tubing in a curve across said curved surface portion to be manually accessible, so that the guide wire forms a pair of S-shaped bends between said bore and the curved manually-accessible portion of the guide wire thereby to inhibit self-ejection of the guide wire from the apparatus.

23. The method of claim 22 further including the step of forming said wrap of elongate tubing as a spiral wrap.

24. The method of claim 22 further including the steps of forming said pair of spaced apart apertures each angulated toward the other to provide a respective surface sloping toward the other of said pair of apertures, and extending the guide wire across the pair of sloping surfaces in the S-shaped bends thereof.

25. The method of claim 22 further including the steps of defining a radially outwardly disposed groove on said elongate tubing and curving about said wrap thereof, forming said groove to extend between said pair of apertures, and receiving the guide wire in said groove to guide the guide wire outwardly on said tubing during manual manipulation thereof.

26. The method of claim 25 further including the step of extruding said elongate tubing to define said radially outwardly disposed groove along the entire length thereof, and spiral wrapping said elongate tubing to dispose said groove radially outwardly, whereby said groove along the entire length of said tubing and between said pair of apertures defines said outer curved surface portion and receives the guide wire in said groove.

27. The method of claim 22 further including the step of forming said wrap of elongate tubing as a spiral wrap.

28. The method of claim 22 further including the step of providing a combined handle and clip member on said apparatus to facilitate manual holding thereof.

29. The method of claim 28 wherein said step of providing a combined handle and clip member on said apparatus includes the steps of providing a clip portion defining at least one recess for captively receiving a wrap of said elongate tubing therein, providing said handle and clip member with a digit-receiving portion disposed within said wrap of tubing, and using said digit-receiving portion to define a recess opening radially inwardly for receiving a finger of a user of said apparatus.

30. The method of claim 29 further including the step of providing said combined handle and clip member with a pair of said digit-receiving portions disposed one behind the other in tandem within said wrap of tubing, and using each of said pair of digit-receiving portions to define a respective recess opening radially inwardly for receiving a respective finger of a user of said apparatus.

31. A storage and dispensing apparatus for a guide wire, said apparatus comprising:

a wrap of elongate tubing having a bore for receiving an elongate guide wire, a first end, a tangential portion extending from said wrap and terminating at an open second end, adjacent to said tangential portion said elongate tubing defining a pair of spaced apart apertures opening from said bore radially outwardly on said tubing, and an outer curved surface portion extending along the length dimension of said tubing intermediate of said pair of openings across which a curved portion of the guide wire may extend and be accessible for manual manipulation to advance and retract the guide wire through said open second end; and a combined handle and clip member including at least one clip portion defining a recess for receiving a wrap of said elongate tubing, said combined handle and clip member including at least a pair of digit-receiving recess portions disposed one behind the other in tandem within said wrap of tubing, each for receiving a respective finger of a user of said apparatus, wherein each of a forward two of said digit-receiving portions defines a respective one of a pair of clip portions extending radially outwardly therefrom, each one of said pair of clip portions extending radially outwardly from the respective one of said pair of pair of digit-receiving portions in general alignment with the respective index and middle fingers of a user of said apparatus and captively retaining at least one wrap of said tubing.

32. A storage and dispensing apparatus for a guidewire in combination with a guidewire, the apparatus designed to prevent uncoiling of the guidewire, the combination comprising:

a wrap of elongate tubing having a bore for receiving an elongate guidewire, a first end, an open second end, and an arcuate exterior surface portion adjacent to the second end and positioned around the wrap of tubing;

a guidewire received within the elongate tubing bore and extending substantially from said first end to said second end within the bore except for in the region of the exterior surface portion where the guidewire passes out of the bore and over the exterior surface portion to be accessible for manual manipulation, the elongate tubing including an aperture on either side of the exterior surface portion so that the guidewire forms two S-turns when leaving and re-entering the bore through the apertures to inhibit self-ejection of the guide wire from the elongate tubing.

33. The combination of claim 32, wherein said apertures each include entrance walls on sides of the apertures closest to the exterior surface portion, the entrance walls being angled to generally conform to the respective angles that the guidewire makes upon leaving and re-entering the bore through the apertures.

34. The combination of claim 32, wherein said elongate tubing defines a radially outwardly disposed groove extending between said apertures, receiving the guide wire, and providing said exterior surface portion across which the guide wire extends between said apertures.

35. The combination of claim 32, further including a combined handle and clip member attached to said wrap of elongate tubing including at least one clip portion defining a recess for receiving a wrap of said tubing.

36. The combination of claim 35, wherein said combined handle and clip member includes at least a pair of said clip portions each defining a respective recess for receiving a respective wrap of said elongate tubing and being spaced circumferentially from one another along said wrap of tubing.

37. The combination of claim 32, further including a tapered introducer tip member removably received at said open second end of said elongate tubing, said introducer tip member defining a bore closely passing the guide wire.

38. The combination of claim 32, wherein said elongate tubing further includes a tangential portion extending from said wrap and being integrally formed into a tapered introducer tip portion defining a bore closely passing the guide wire and also defining said open second end of said elongate tubing.

* * * * *